US008439975B2

(12) United States Patent
He et al.

(10) Patent No.: US 8,439,975 B2
(45) Date of Patent: May 14, 2013

(54) POLYETHYLENE CROSS-LINKED WITH AN ANTHOCYANIN

(71) Applicant: Howmedica Osteonics Corp., Mahwah, NJ (US)

(72) Inventors: Shulin He, Montvale, NJ (US); Shi-Shen Yau, Berkeley Heights, NJ (US); Aiguo Wang, Wayne, NJ (US); Daniel E. Lawrynowicz, Monroe, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/623,254

(22) Filed: Sep. 20, 2012

(65) Prior Publication Data

US 2013/0064711 A1    Mar. 14, 2013

Related U.S. Application Data

(60) Division of application No. 13/115,451, filed on May 25, 2011, now Pat. No. 8,303,657, which is a continuation of application No. 12/221,678, filed on Aug. 5, 2008, now Pat. No. 8,133,436.

(51) Int. Cl.
*A61F 2/02* (2006.01)

(52) U.S. Cl.
USPC ................. 623/11.11; 623/23.56

(58) Field of Classification Search ........ 623/11.11, 623/23.56; 422/22; 250/492.1, 492.3
See application file for complete search history.

(56) References Cited

U.S. PATENT DOCUMENTS

| | | | |
|---|---|---|---|
| 4,118,516 A | 10/1978 | Van Praag et al. |
| 4,150,485 A | 4/1979 | Lee, Jr. et al. |
| 4,678,436 A | 7/1987 | Kondo et al. |
| 4,729,834 A | 3/1988 | Itoh et al. |
| 4,910,259 A | 3/1990 | Kindt-Larsen et al. |
| 5,039,536 A | 8/1991 | Vunsh et al. |
| 5,414,049 A | 5/1995 | Sun et al. |
| 5,814,049 A | 9/1998 | Pratt et al. |
| 5,827,904 A | 10/1998 | Hahn |
| 5,985,636 A | 11/1999 | Gray et al. |
| 6,194,469 B1 | 2/2001 | Nair et al. |
| 6,277,390 B1 | 8/2001 | Schaffner et al. |
| 6,316,158 B1 | 11/2001 | Saum et al. |
| 6,448,315 B1 | 9/2002 | Lidgren et al. |
| 6,518,356 B1 | 2/2003 | Friese et al. |
| 6,756,421 B1 | 6/2004 | Todo et al. |
| 6,818,020 B2 | 11/2004 | Sun et al. |
| 7,091,260 B2 | 8/2006 | K hn |
| 7,132,296 B2 | 11/2006 | Ou et al. |
| 7,199,180 B1 | 4/2007 | Simmons et al. |
| 7,214,764 B2 | 5/2007 | King |
| 7,275,932 B2 | 10/2007 | Jin et al. |
| 7,304,097 B2 | 12/2007 | Muratoglu et al. |
| 7,335,697 B2 | 2/2008 | King et al. |
| 7,431,874 B2 | 10/2008 | Muratoglu et al. |
| 7,498,365 B2 | 3/2009 | Muratoglu et al. |
| 2002/0156483 A1 | 10/2002 | Voellmicke et al. |
| 2002/0164434 A1 | 11/2002 | Tarvin et al. |
| 2004/0156879 A1 | 8/2004 | Muratoglu et al. |
| 2005/0043431 A1 | 2/2005 | Wang et al. |
| 2005/0154081 A1 | 7/2005 | Yin et al. |
| 2005/0194722 A1 | 9/2005 | Muratoglu et al. |
| 2005/0194723 A1 | 9/2005 | Muratoglu et al. |
| 2005/0203217 A1 | 9/2005 | Pomrink |
| 2005/0256220 A1 | 11/2005 | Lavergne et al. |
| 2006/0094077 A1 | 5/2006 | Kanner et al. |
| 2006/0264541 A1 | 11/2006 | Lederer et al. |
| 2006/0293407 A1 | 12/2006 | Kuhn et al. |
| 2007/0059334 A1 | 3/2007 | Abt et al. |
| 2007/0077268 A1 | 4/2007 | King et al. |
| 2007/0128242 A1 | 6/2007 | Zhao |
| 2007/0260325 A1 | 11/2007 | Wenz |
| 2008/0260821 A1 | 10/2008 | Mumper et al. |
| 2010/0274282 A1 | 10/2010 | Olson |

FOREIGN PATENT DOCUMENTS

| | | |
|---|---|---|
| CS | 221403 | 4/1983 |
| EP | 542108 | 5/1993 |
| EP | 613923 | 9/1994 |
| EP | 805178 | 11/1997 |
| EP | 995449 | 4/2000 |
| EP | 995450 | 4/2000 |
| EP | 1779877 | 5/2007 |
| GB | 2 180 815 A1 | 4/1987 |
| WO | 2004101009 | 11/2004 |
| WO | 2006108167 | 10/2006 |
| WO | 2007038421 | 4/2007 |
| WO | 2008006890 | 1/2008 |

OTHER PUBLICATIONS

Radiation Effects on Polymers, American Chemical Society, 1991 (Symposium of Aug. 26-31, 1990) pp. 89-92.
Website printout, Anthocyanin—wikipedia, the free encyclopedia, en.wikipedia.org, 7 pages, printed Sep. 17, 2007.
Website printout, anthocyanin Molecule, www.worldofmolecules.com, Anthocyanins, 4 pages, printed Sep. 17, 2007.

*Primary Examiner* — Sean E Conley
(74) *Attorney, Agent, or Firm* — Lerner, David, Littenberg, Krumholz & Mentlik, LLP

(57) ABSTRACT

A method for manufacturing of ultrahigh molecular weight polyethylene (UHMWPE) for implants, where the implants have been machined out of UHMWPE blocks or extruded rods, has anthocyanin dispersely imbedded in the polyethylene. The implant is then exposed to γ ray or electron beam irradiation in an amount of at least 2.5 Mrad followed by a heat treatment to prevent the implant from becoming brittle in the long term as well as to improve strength and wear. The method includes mixing a powder or granulate resin of UHMWPE with an aqueous liquid that contains anthocyanin in a predetermined amount. The water is then evaporated to deposit the anthocyanin in a predetermined concentration on the polyethylene particles. The doped UHMWPE particles are compressed into blocks at temperatures in a range of approximately 135° C.-250° C. and pressures in a range of approximately 2-70 MPa. Medical implants are made from the blocks.

17 Claims, No Drawings

POLYETHYLENE CROSS-LINKED WITH AN ANTHOCYANIN

CROSS-REFERENCE TO RELATED APPLICATIONS

The present application is a divisional of U.S. patent application Ser. No. 13/115,451, filed on May 25, 2011, which is a continuation of U.S. patent application Ser. No. 12/221,678, filed on Aug. 5, 2008, which issued as U.S. Pat. No. 8,133,436 on Mar. 13, 2012, the disclosures of which are incorporated herein by reference.

BACKGROUND OF THE INVENTION

This invention relates to medical implants formed of a polymeric material such as ultra-high molecular weight polyethylene (UHMWPE), with superior oxidation and wear resistance produced by an irradiation process. The UHMWPE is doped with the anti-oxidant anthocyanin.

Various polymer systems have been used for the preparation of artificial prostheses for biomedical use, particularly orthopedic applications. Among them, ultra-high molecular weight polyethylene is widely used for articulation surfaces in artificial knee, hip, and other joint replacements. Ultra-high molecular weight polyethylene (UHMWPE) has been defined as those linear polyethylenes which have a relative viscosity of 2.3 or greater at a solution concentration of 0.05% at 135° C. in decahydronaphthalene. The nominal weight–average molecular weight is at least 400,000 and up to 10,000,000 and usually from three to six million. The manufacturing process begins with the polymer being supplied as fine powder which is consolidated into various forms, such as rods and slabs, using ram extrusion or compression molding. Afterwards, the consolidated rods or slabs are machined into the final shape of the orthopedic implant components. Alternatively, the component can be produced by compression molding of the UHMWPE resin powder.

All components must then go through a sterilization procedure prior to use, but usually after being packaged. There exist several sterilization methods which can be utilized for medical applications, such as the use of ethylene oxide, gas plasma, heat, or radiation. However, applying heat to a packaged polymeric medical product can destroy either the integrity of the packaging material (particularly the seal, which prevents bacteria from going into the package after the sterilization step) or the product itself.

It has been recognized that regardless of the radiation type, the high energy beam causes generation of free radicals in polymers during radiation. It has also been recognized that the amount or number of free radicals generated is dependent upon the radiation dose received by the polymers and that the distribution of free radicals in the polymeric implant depends upon the geometry of the component, the type of polymer, the dose rate, and the type of radiation beam. The generation of free radicals can be described by the following reaction (which uses polyolefin and gamma ray irradiation for illustration):

$$\text{Polyolefin} \xrightarrow{\text{gamma rays}} \text{r• where r• are primary free radicals *} \quad (1)$$

* (through C-C chain scission or C-H scission)

Depending on whether or not oxygen is present, primary free radicals r· will react with oxygen and the polymer according to the following reactions as described in "Radiation Effects on Polymers," edited by Roger L. Clough and Shalaby W. Shalaby, published by American Chemical Society, Washington, D.C., 1991.

In the presence of oxygen $$O_2 r\bullet \longrightarrow rO_2 \quad (2)$$

$$rO_2 + \text{polyolefin} \longrightarrow rOOH + P\bullet \quad (3)$$

$$P\bullet + O_0 \longrightarrow PO_2\bullet \quad (4)$$

$$PO_2\bullet + \text{polyolefin} \longrightarrow POOH + P\bullet \xrightarrow{O_2} PO_2\bullet \quad (5)$$

$$rO_2\bullet, PO_2\bullet \longrightarrow \text{Some chain scission products} \quad (6)$$

$$rOOH, POOH \xrightarrow{\text{room temperature}} \text{free radicals, rOH, POH} \quad (7)$$

$$P\bullet + PO_2 \longrightarrow POOP \text{ (ester cross-links)} \quad (8)$$

$$2 P\bullet \longrightarrow P\text{-}P \text{ (C-C cross-links)} \quad (9)$$

In radiation in air, primary free radicals r· will react with oxygen to form peroxyl free radicals $rO_2$·, which then react with polyolefin (such as UHMWPE) to start the oxidative chain scission reactions (reactions 2 through 6). Through these reactions, material properties of the plastic, such as molecular weight, tensile and wear properties, are degraded.

It has been found that the hydroperoxides (rOOH and POOH) formed in reactions 3 and 5 will slowly break down as shown in reaction 7 to initiate post-radiation degradation. Reactions and 9 represent termination steps of free radicals to form ester or carbon-carbon cross-links. Depending on the type of polymer, the extent of reactions 8 and 9 in relation to reactions 2 through 7 may vary. For irradiated UHMWPE, a value of 0.3 for the ratio of chain scission to cross-linking has been obtained, indicating that even though cross-linking is a dominant mechanism, a significant amount of chain scission occurs in irradiated polyethylene.

By applying radiation in an inert atmosphere, since there is no oxidant present, the primary free radicals r. or secondary free radicals P. can only react with other neighboring free radicals to form carbon-carbon cross-links, according to reactions 10 through 12 below. If all the free radicals react through reactions 10 through 12, there will be no chain scission and there will be no molecular weight degradation. Furthermore, the extent of cross-linking is increased over the original polymer prior to irradiation. On the other hand, if not all the free radicals formed are combined through reactions 10, 11 and 12, then some free radicals will remain in the plastic component.

In an Inert Atmosphere

| | |
|---|---|
| r• + polyolefin ---------- P• | (10) |
| 2 r• ---------- r-r (C-C cross-linking) | (11) |
| 2 P• ---------- P P (C-C cross-linking) | (12) |

It is recognized that the fewer the free radicals, the better the polymer retains its physical properties over time. The greater the number of free radicals, the greater the degree of molecular weight and polymer property degradation will occur. Applicant has discovered that the extent of completion of free radical cross-linking reactions is dependent on the reaction rates and the time period given for reaction to occur.

UHMWPE is commonly used to make prosthetic joints such as artificial hip joints. In recent years, it has been found that tissue necrosis and interface osteolysis may occur in response to UHMWPE wear debris. For example, wear of acetabular cups of UHMWPE in artificial hip joints may introduce microscopic wear particles into the surrounding tissues.

Improving the wear resistance of the UHMWPE socket and, thereby, reducing the rate of production of wear debris may extend the useful life of artificial joints and permit them to be used successfully in younger patients. Consequently, numerous modifications in physical properties of UHMWPE have been proposed to improve its wear resistance.

It is known in the art that ultra-high molecular weight polyethylene (UHMWPE) can be cross-linked by irradiation with high energy radiation, for example gamma radiation, in an inert atmosphere or vacuum. Exposure of UHMWPE to gamma irradiation induces a number of free-radical reactions in the polymer. One of these is cross-linking. This cross-linking creates a 3-dimensional network in the polymer which renders it more resistant to adhesive wear in multiple directions. The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in an increase in the wear rate as a result of oxidation over the life of the implant.

Sun et al. U.S. Pat. No. 5,414,049, the teachings of which are incorporated herein by reference, broadly discloses the use of radiation to form free radicals and heat to form cross-links between the free radicals prior to oxidation.

Hyun et al. U.S. Pat. No. 6,168,626 relates to a process for forming oriented UHMWPE materials for use in artificial joints by irradiating with low doses of high-energy radiation in an inert gas or vacuum to cross-link the material to a low degree, heating the irradiated material to a temperature at which compressive deformation is possible, preferably to a temperature near the melting point or higher, and performing compressive deformation followed by cooling and solidifying the material. The oriented UHMWPE materials have improved wear resistance. Medical implants may be machined from the oriented materials or molded directly during the compressive deformation step. The anisotropic nature of the oriented materials may render them susceptible to deformation after machining into implants.

Salovey et al. U.S. Pat. No. 6,228,900, the teachings of which are incorporated by reference, relates to a method for enhancing the wear-resistance of polymers, including UHMWPE, by cross-linking them via irradiation in the melt.

Saum et al. U.S. Pat. No. 6,316,158 relates to a process for treating UHMWPE using irradiation followed by thermally treating the polyethylene at a temperature greater than 150° C. to recombine cross-links and eliminate free radicals.

Several other prior art patents attempt to provide methods which enhance UHMWPE physical properties. European Patent Application 0 177 522 81 relates to UHMWPE powders being heated and compressed into a homogeneously melted crystallized morphology with no grain memory of the UHMWPE powder particles and with enhanced modulus and strength. U.S. Pat. No. 5,037,928 relates to a prescribed heating and cooling process for preparing a UHMWPE exhibiting a combination of properties including a creep resistance of less than 1% (under exposure to a temperature of 23° C. and a relative humidity of 50% for 24 hours under a compression of 1000 psi) without sacrificing tensile and flexural properties. U.K. Patent Application GB 2 180 815 A relates to a packaging method where a medical device which is sealed in a sterile bag, after radiation/sterilization, is hermetically sealed in a wrapping member of oxygen-impermeable material together with a deoxidizing agent for prevention of post-irradiation oxidation.

U.S. Pat. No. 5,153,039 relates to a high density polyethylene article with oxygen barrier properties. U.S. Pat. No. 5,160,464 relates to a vacuum polymer irradiation process.

In addition to cross-linking via a stabilization or annealing process, it is possible to chemically cross-link the polyethylene. However, when implanting a polyethylene in the human body it is necessary to chemically cross-link with a non-toxic chemical. U.S. Pat. No. 5,827,904 relates to the use of a carotenoid doped into a powder base or stock solid polyethylene material to produce a stabile oxidation resistant matrix for use in medical implants. U.S. Pat. No. 6,277,390 teaches the use of vitamin E (alpha-tocopherol) to protect from irradiation damage. U.S. Patent Application Publication No. 2006/0264541 and U.S. Patent Application Publication No. 2007/0059334 also relate to utilizing vitamin E to stabilize UHMWPE. U.S. Pat. No. 6,448,315 relates to a method using $CO_2$ under super critical fluid conditions at elevated temperatures and pressures to dope the UHMWPE with vitamin E. Sequentially irradiating and annealing is taught in U.S. Patent Publication No. 2005/0043431. U.S. Patent Application Publication No. 2005/0194723 also relates to methods for making medical devices having vitamin E diffused therein.

BRIEF SUMMARY OF THE INVENTION

The present invention relates to a method for providing a polymeric material, such as UHMWPE, with superior oxidation resistance, mechanical strength and wear properties. For the purpose of illustration, UHMWPE will be used as an example to describe the invention. However, all the theories and processes described hereafter should also apply to other polymeric materials such as polypropylene, high density polyethylene, polyhydrocarbons, polyester, nylon, polyurethane, polycarbonates and poly(methylmethcrylate) unless otherwise stated. The method involves using a series of relatively low doses of radiation with an annealing process after each dose.

As stated above, UHMWPE polymer is very stable and has very good resistance to aggressive media except for strong oxidizing acids. Upon irradiation, free radicals are formed which cause UHMWPE to become activated for chemical reactions and physical changes. Possible chemical reactions include reacting with oxygen, water, body fluids, and other chemical compounds while physical changes include density, crystallinity, color, and other physical properties. In the present invention, an anthocyanin compound is used to eliminate the free radicals during irradiation. Furthermore, this process does not employ stabilizers, antioxidants, or any other chemical compounds which may have potentially adverse effects in biomedical or orthopedic applications.

An orthopedic preformed material such as a rod, bar or compression molded sheet for the subsequent production of a medical implant such as an acetabular or tibial implant with improved wear resistance is made from a polyethylene material doped with an anthocyanin in a concentration of up to 5% wt/wt. The material is cross-linked by a total radiation dose of from about 2 MRads to 100 MRads and preferably between 5 MRads and 15 MRads and most preferably 9-12 MRads.

The polyethylene of the present invention may be in the form of a preformed rod or sheet with a subsequent production of a medical implant with improved wear resistance. The preformed rod or sheet doped with an anthocyanin is cross-linked by irradiation one or more times. The preferred method is to apply the radiation dose in increments, the incremental dose for each radiation is preferably between about 2 and 5 MRads with the total dose between 2 and 100 MRads and preferably between 5 and 21 MRads and most preferably 9 and 12 MRads.

A first method of forming a cross-linked ultra-high molecular weight polyethylene blend comprises: combining an anthocyanin material and ultra-high molecular weight polyethylene to form a doped ultra-high-molecular weight polyethylene; and sequentially irradiating the ultra-high molecular weight polyethylene blend with electron-beam or gamma ray radiation to a total dose of at least about 2 MRad and preferably 9-12 MRads to form a cross-linked ultra-high-molecular weight polyethylene blend. The amount of anthocyanin combined in the blend is preferably between about 0.002 w/w % and about 2.0 w/w %. Even more preferably the amount of anthocyanin combined in the blend is between about 0.005 and about 0.4 w/w %.

The preferred method further comprises the step of heating the ultra-high molecular weight polyethylene doped with anthocyanin after each irradiation. Preferably the temperature is between 110° C. and 130° C. but less than the melting point for about 8 hours. This sequential radiation and annealing process is taught in U.S. Patent Publication No. 2004/0043431, the disclosure of which is incorporated herein by reference. The cross-linked ultra-high molecular weight doped polyethylene may be formed into an implant such as by molding. The implant is sterilized during or subsequent to irradiating. Preferably the sterilizing step comprises contacting the implant with electron-beam radiation, gamma radiation, gas plasma or ethylene oxide. After sterilization the implant is packaged in a sterile container. The sterilizing step may occur during, after or both during and after packaging the implant. The ultra high molecular weight polyethylene doped with anthocyanin is a substantially uniform blend.

A second method of forming a sterilized packaged implant comprises: forming an implant from a resin blend of ultra-high molecular weight polyethylene and anthocyanin such as by molding or extrusion and then packaging the implant. The packaged implant is then irradiated with electron-beam radiation to a total dose of at least about 2 MRad and preferably 9 to 12 MRads at a dose rate of at least about 0.5 MRAD per hour. The irradiation may be done in one step or preferably sequentially. Preferably the implant is packaged in an oxygen-deprived barrier package and the ultra-high molecular weight doped polyethylene is a substantially uniformly blended mixture.

The methods produce a load bearing medical implant, comprising: a solid UHMWPE material; and a sufficient amount of anthocyanin compound doped into the polymeric solid material to produce a stable, oxidation resistant, matrix for forming the medical, load bearing implant. The anthocyanin compound is preferably present in a range of from 0.002 w/w % amounts to 2% by weight. The blended resin composition may be formed into a polymeric solid material in a rod bar or block stock form by extrusion or preferably by molding. The implant made of the UHMWPE is machined out of UHMWPE blocks or extruded bars or rods, wherein anthocyanin is dispersely imbedded in the polyethylene with a preferred concentration K of $0.002\% < K < 2\%$. The doped implant is exposed to gamma ray or electron beam irradiation amounts of at least about 2.0 MRad to prevent the implant from becoming brittle in the long term and improve wear properties.

The implant may be manufactured from doped UHMWPE, where the implants have been machined out of doped UHMWPE blocks or extruded bars or rods, wherein anthocyanin is dispersely imbedded in the polyethylene with a concentration K of $0.002\% < K < 2\%$, the implant being exposed to gamma ray or electron beam irradiation in amounts of 9 to 12 MRad and annealed after irradiation. Preferably this is done sequentially as described in U.S. Patent Publication No. 2004/0043431. The anthocyanin prevents the implant from becoming brittle in the long term and thereby wear and tear at contact locations. The inclusion of anthocyanin is preferably by mixing a powder or granulate of UHMWPE with an aqueous liquid such as deionized water that contains anthocyanin (which is water soluble) in a predetermined amount. The water is evaporated in order to deposit the anthocyanin in a predetermined concentration on the polyethylene particles. The polyethylene particles are compressed into blocks at temperatures in a range of approximately 135° C.-250° C. and pressures in a range of approximately 2-70 MPa.

The preformed doped polyethylene material is then machined into a medical implant or other device. If the irradiation process takes place in air, then the entire outer skin to about 2 mm deep is removed from the preform prior to machining the medical implant or other device. If the process is done in a vacuum or an inert atmosphere such as nitrogen, then the outer skin may be retained.

The end-results of reduced chain-scission and free-radical concentration are improved mechanical properties, improved oxidation resistance and enhanced wear resistance.

DETAILED DESCRIPTION

Anthocyanins are water soluble naturally occurred products. They are present in plants, flowers, fruits such as grapes, berries and in red wine. Anthocyanins are natural pigments that appear red, purple to blue according to pH. Importantly, anthocyanins act as powerful antioxidants to protect the plant from free radical induced oxidation. Their antioxidant capacity could be up to 4 times higher than Vitamin E. Anthocyanins have also been found to have anti-inflammability, anti-angiogenic and anti-carcinogenic properties. Currently anthocyanins are widely used in the food industry.

Two anthocyanin extracts in powder form from grape skin (Antho-G) and bilberry (Antho-B) respectively and a total of four concentrations were tested: The anthocyanin extract (Antho-G) from grape skin was obtained from Food Ingredient Solution LLC as a food additive. Anthocyanin content in the grape extract is about 8%. The anthocyanin extract from bilberry (Antho-B) was obtained from Charles Bowman and Company and anthocyanin content in the bilberry extract is 50%.

The anthocyanin extract used was obtained as a red powder. In the preferred method the red powder was dissolved in water at appropriate concentrations. A solution of 2.5% of either extract was used. The mixing formed a red aqueous solution. Typically, 16 ml of the 2.5% solution of either Antho-G or Antho-B was added to 800 g UHMWPE powder and the mixture was blended using a Papenmeier shear blender. The doped powder wet mixture (light pink depending on the concentration of anthocyanin) was dried under nitrogen and then consolidated at 350° F., with a maximum unit pressure of approximately 1000 psi (34 MPa). A pinkish colored UHMWPE block in a size of 2×3×6 inches was obtained in a custom Wabash 4 opening press.

Alternately, 0.4 grams of dry anthocyanin (Ortho-G or Antho-B) red powder could be blended with 800 UHMWPE powder. This will result in a similar colored UHMWPE powder as was obtained with the wet blended powder. Molding would be performed as described above.

The content of anthocyanin in the UHMWPE may be up to 5% by weight and preferably 0.005 to 2% by weight. The color of the UHMWPE got deeper from pink to dark red with an increase of anthocyanin content.

The UHMWPE may be formed into a block by compression molding and the block with anthocyanin was gamma irradiated at an approximately 9 MRad in three steps with annealing after each step of cumulated doses. The color of the UHMWPE was visually examined and no color change was observed.

EXAMPLE

Gur 1020 brand UHMWPE powder per ASTM F 648 Type I was purchased from Ticona GmbH, FrankfurtMain, Germany. The partial size of the powder was less than 300 μm.

The anthocyanin Antho-G and Antho-B extracts were dissolved in water in a concentration of 2.5% and mixed into the UHMWPE powder using a Papenmeier shear blender. The amount of the 2.5% solution added to the UHMWPE powder was varied to produce either 500 ppm (0.05% w/w) or 250 ppm (0.025% w/w) of the antho-G extract or 250 or 125 ppm of the antho-B extract. The actual concentration of anthocyanin contained in each sample is shown in Table 1. After drying under nitrogen, the UHMWPE blend was then molded at 350° F. and with a maximum unit pressure of approximately 1000 psi (4 MPa) to produce a test sample plaque in a size of 2×3×6 inches.

The anthocyanin doped plaques were sequentially gamma irradiated 3 MRad for a total dose of 9 and annealed after each dose at 130° C. for 8 hours. Test samples (1 mm slices) were then machined out of the treated blocks and tested according to the ASTM standard methods.

The density measurements were determined according to ASTM D1505 using density gradient column. Two (2) specimens per sample were evaluated. Average value and standard deviation are reported.

Crystallinity measurements were obtained in accordance with ASTM D3418. Standard testing on Perkin-Elmer Diamond DSC was used. Both heating and cooling runs were performed at 10° C./min. The peak temperature on the heating and the cooling curves determined the melting point and the crystallization temperature, respectively. The crystallinity was calculated as the heat of fusion of the test specimen divided by 287.3 J/g (the heat of fusion for a perfect PE crystal). Five (5) specimens per sample were analyzed; the average value and standard deviation are reported. A virgin GUR 1020 sample was included in every run for control. The results of the analysis are shown in Table 1.

The tensile test was conducted according to ASTM D638 (Reference 3), Type IV with a crosshead speed set at 5.08 cm/min (or 2 in/min). A standard tensile tester (Instron 4505) was used. Eight specimens per sample condition were tested; the average value and standard deviation are reported for yield strength, ultimate strength and elongation. The results are shown in Table 1.

TABLE 1

Physical and mechanical properties of anthocyanin UHMWPE

| Material Property | Undoped Reference | Antho-G 500 ppm of Extract | Antho-G 250 ppm of Extract | Antho-B 250 ppm of Extract | Antho-B 125 ppm of Extract |
|---|---|---|---|---|---|
| Density, kg/m3 | 939 | 938 | 939 | 937 | 939 |
| Crystallinity (*) % | 59.2 ± 1.2 | 58.6 ± 0.7 | 61.2 ± 3.4 | 57.3 ± 0.1 | 59.0 ± 0.8 |
| Tensile Yield Strength, MPa | 23.8 ± 0.2 | 24.2 ± 0.2 | 24.1 ± 0.2 | 23.9 ± 0.2 | 23.5 ± 0.3 |
| Tensile Ultimate Strength, MPa | 54.0 ± 4.4 | 52.9 ± 3.5 | 56.6 ± 2.4 | 58.2 ± 2.9 | 55.3 ± 3.5 |
| Tensile Elongation at Break, % | 268 ± 13 | 262 ± 12 | 272 ± 7 | 278 ± 8.8 | 270 ± 9.2 |
| Anthocyanin concentration (PPM) | 0 | 40 PPM | 20 PPM | 125 PPM | 62.5 PPM |

Physical and mechanical properties of the anthocyanin doped UHMWPE are shown in Table 1. The data indicate that addition of the anthocyanin extract resulting in either a 125, 250 ppm (0.0125% w/w) or 500 ppm (0.05% w/w) concentration of extract in the GUR 1020 did not affect the physical and mechanical properties.

Free radical measurements were conducted at the Department of Physics, The University of Memphis. The experiment procedures are as follows: Following machining/cutting, each sample was cleaned in ethanol and dried in a drying environment using filtered dry nitrogen. However, precut/pre-machined, cleaned and prepackaged samples are used without any additional cleaning. Before measurements, the mass of each sample was recorded using a microgram scale (GA 110, Ohaus). The sample for measurement was placed in a high purity suprasil quartz tube of size 4 mm outer and 3 mm inner diameters, and varying between 100 and 200 mm in length (Wilmad Glass). Along with each sample, a reference standard (SRM 2601, NIST) was also placed in the tube. For free radical measurements, an X-band electron spin resonance (ESR) spectrometer (EMX 300, Bruker) was used. The spectrometer operates at around 9.7 GHz (empty cavity frequency), it was fitted with a multimode high-sensitive cavity (Bruker), and was fully automated. Experimental resonance frequency, which was factored into the calculation for the spectral g value (characteristic splitting factor of a spectrum), was automatically recorded as an operating parameter when the cavity was tuned with the tube-with-sample in place. ESR signal was detected as the first derivative of the resonance absorption by setting the frequency of the magnetic field modulation and that of the signal detection at 100 kHz. In general, the amplitude of modulation (1-5 G) and that of the microwave power (0.5-5.0 mW) were preset to obtain desired signal-to-noise ratio and to keep the detection range below saturation level of the absorption signal. For spectral discrimination, however, modulation amplitude was varied between 1 mG and 20 G, and the microwave power between 1.0 mW and 100 mW, respectively, as needed. First-derivative absorption signal of the reference standard was also recorded at the same time without re-tuning the cavity or altering any operating parameters of the spectrometer. Spectral data as well as the operating parameters are automatically recorded by a dedicated PC, and subsequent calculations or presentations were performed using a WinEPR program (Bruker).

Using the known number of free spins in the standard, free-radical concentration (FRC) in the sample was determined. The results are shown in Table 2.

Table 2 Free radical data

| Sample | FRC (Spins per gram, x E-14) |
|---|---|
| Antho-G-500 PPM | 5.99 |
| Antho-G-250 PPM | 17.07 |
| Antho-B-250 PPM | 11.68 |
| Antho-B-125 PPM | 10.45 |
| Reference (undoped) | 11.31 |

An accelerated aging test was conducted following the standard method described in ASTM2102. UHMWPE without antioxidant (reference), which was gamma irradiated sterilized at 3 MRads in either air (gamma-air) or nitrogen (N2) respectively, were used as references. The aged specimens were analyzed by FTIR and the data are shown in Table 3.

TABLE 3

Oxidation index (OI) of the anthocyanin doped UHMWPE after two weeks accelerated aging

| Sample | Max OI | | SOI (0-3 mm) | | BOI (0.5 mm) | |
|---|---|---|---|---|---|---|
| | 2 wks | 4 wks | 2 wks | 4 wks | 2 wks | 4 wks |
| Antho-G-500 ppm | 0.00 | 0.00 | 0.00 | 0.00 | 0.00 | 0.00 |
| Antho-G- 250 ppm | 0.00 | 0.00 | 0.00 | 0.00 | 0.00 | 0.00 |
| Antho-B-250 ppm | 0.00 | 0.01 | 0.00 | 0.00 | 0.00 | 0.00 |
| Antho-B- 125 ppm | 0.00 | 0.00 | 0.00 | 0.00 | 0.00 | 0.00 |
| Reference Gamma irradiated in Air | 0.56 | | 0.35 | | 0.22 | |
| Reference Gamma irradiated in N2 | 0.34 | | 0.19 | | 0.30 | |

Max OI: maximum oxidation index;
SOI: average surface oxidation index;
BOI: average bulk oxidation index;
2wks: 2 weeks (ASTM standard);
4wks: 4 weeks.

The results demonstrate that no oxidation was detected in the anthocyanin doped specimens after two weeks accelerated aging. The oxidation was found through the entire range of specimens of the two references. When the accelerated aging was extended to four weeks, there was still no oxidation detected in the anthocyanin doped sample.

Wear testing was conducted on the acetabular cups with an inner diameter of 32 mm, and a thickness of 5.9 mm. Inserts were manufactured from four anthocyanin doped UHMWPE. All samples were inserted into titanium acetabular shells which are mounted to UHMWPE fixtures using titanium bone screws. Appropriate diameter CoCr femoral heads were mated against the inserts. A multi-station MTS (Eden Prairie, Minn.) hip joint wear simulator was used for testing.

Reference UHMPE materials included: (1) undoped UHMWPE and UHMWPE doped with 500 PPM vitamin E using a powder-liquid blending process. All materials were gamma irradiated at 3 MRads and then annealed at 130° C. for 8 hours. This was done sequentially three times for a total of 9 MRads.

The test specimens were submerged in a lubricant bath for the duration of testing. Alpha Calf Fraction serum was used. After diluted and protein adjusted, the serum solution was 0.2 μm filed before use. The standard method described in ASTM F2025-06 was used for cleaning, weighing and assessing the wear loss of the acetabular inserts. The serum solution was replaced and the inserts weighed every 0.5 million cycles. Testing was conducted for a minimum of 2 million cycles.

Wear rates were determined based on the weight loss of the specimens during testing. The weight loss of the specimens was corrected by fluid absorption that was done by monitoring the weight gain of the static soaked specimens.

TABLE 4

Wear rates of anthocyanin doped UHMWPE after two million cycles on a hip join stimulator

| | Wear rate ($mm^3$/mc) |
|---|---|
| Antho-G-500 ppm | 1.3 ± 0.1 |
| Antho-G-250 ppm | 3.3 ± 1.3 |
| Antho-B-250 ppm | 1.4 ± 1.5 |
| Antho-B-125 ppm | 2.2 ± 0.6 |
| UHMWPE-vitamin E 500 PPM | 6.0 ± 0.4 |
| UHMWPE undoped | 2.9 ± 0.3 |

Table 4 shows the wear rates of the anthocyanin doped UHMWPE after two million cycles on a hip joint stimulator. Lower wear rates were seen in the UHMWPE doped with high concentrations of the anthocyanin (Antho-G 500 PPM and Antho-B 250 PPM). Compared to the 500 PPM vitamin E doped UHMWPE and undoped UHMWPE that were processed and fabricated under the same conditions. The anthocyanin doped UHMWPE had lower wear rates and better wear resistance.

It is well known that antioxidants will react with free radicals during the irradiation-crosslinking process; this reduces the availability of free radicals in UHMWPE for crosslinking. However, the above results demonstrated that the addition of anthocyanin will improve wear resistance of crosslinked UHMWPE. The UHMWPE containing anthocyanin showed a lower wear rate than undoped UHMWPE that received the same irradiation crosslink and heat treatment. All UHMWPE containing anthocyanin showed significant ($p<0.011$) lower wear than that with 500 ppm vitamin E doped UHMWPE.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of making cross-linked ultra-high molecular weight polyethylene material comprising:
    combining a solution of anthocyanin material and ultra-high molecular weight polyethylene (UHMWPE) powder to form a doped ultra-high-molecular weight polyethylene wherein the anthocyanin is uniformly blended with the UHMWPE powder after drying; and
    consolidating the doped powder to form a material having a color from light pink to deep red.

2. The method as set forth in claim 1 wherein the concentration of anthocyanin is between 0.005 and 5% by weight.

3. The method as set forth in claim 2 wherein a pink color is produced by a concentration of 0.005 by weight.

4. The method as set forth in claim 2 wherein the anthocyanin and the UHMWPE powder is blended in a blender prior to drying.

5. The method as set forth in claim 1 wherein the blend is dried under nitrogen.

6. The method of claim 1 further comprising the step of irradiating the consolidated doped UHMWPE and heating the doped UHMWPE after irradiating.

7. The method of claim 6 further comprising the step of forming the irradiated and heated doped ultra-high molecular weight polyethylene into an orthopedic bearing component.

8. The method of claim 6 further comprising the step of sterilizing the consolidated doped UHMWPE during or subsequent to irradiating.

9. The method of claim 8 wherein the sterilizing step comprises contacting the implant with electron-beam radiation, gamma radiation, gas plasma or ethylene oxide.

10. The method of claim 1 wherein the ultra high molecular weight polyethylene anthocyanin blend is a substantially uniform blend.

11. A method of forming a sterilized packaged medical implant comprising:
    blending an ultra-high molecular weight polyethylene (UHMWPE) powder and an anthocyanin solution wherein the anthocyanin is dispersed in the UHMWPE in a concentration of between 0.05% and 5.0% w/w % to form a uniform blend having a color of light pink to deep red;
    consolidated the blended polyethylene powder;
    thereafter forming a medical implant; and
    sterilizing the formed medical implant.

12. The method of claim 11 wherein the sterilizing step comprises contacting the implant with electron-beam radiation, gamma radiation, gas plasma or ethylene oxide.

13. The method as set forth in claim 11 further comprising irradiating and heating the consolidated blended polyethylene powder.

14. A method of making ultra high molecular weight polyethylene (UHMWPE) material comprising:
    mixing a power or granulate of UHMW polyethylene with an aqueous liquid that contains anthocyanin in a concentration of between 0.002% and 5.0% by weight, the liquid having a color from light pink to deep red;
    evaporating the aqueous liquid in order to deposit the anthocyanin in a predetermined concentration on the polyethylene particles;
    compressing the coated polyethylene particles into blocks or rods at temperatures in a range of approximately 135° C.-250° C. and pressures in a range of approximately 2-70 Mpa and
    sequentially irradiating the blocks or rods at a dose of 2-5 Mrads for a total dose of 9-12 Mrads followed by heating below the melting point followed by cooling after each irradiation to produce a material having a color of light pink to red.

15. The method as set forth in claim 14 wherein the aqueous liquid comprises deionized water.

16. The method as set forth in claim 14 further comprising forming the material into medical implants.

17. The method as set forth in claim 14 wherein the anthocyanin is obtained from grapes or bilberries.

* * * * *